United States Patent [19]
Schwenn et al.

[11] Patent Number: 5,538,499
[45] Date of Patent: Jul. 23, 1996

[54] ORTHOPAEDIC SHOULDER BRACE HAVING ADJUSTABLE PELVIC, SCAPULARY, AND ARM SUPPORTS

[75] Inventors: Shannon R. Schwenn, Orlando, Fla.; Bryan J. Puch, Boulder, Colo.; Mark Glover, Troy, Mich.

[73] Assignee: Orthomerica Products, Inc., Newport Beach, Calif.

[21] Appl. No.: 250,299

[22] Filed: May 27, 1994

[51] Int. Cl.$^6$ ........................................ A61F 5/00
[52] U.S. Cl. .................. 602/20; 602/19; 602/16
[58] Field of Search .............................. 602/4, 5, 16, 20, 602/21, 19; 128/878

[56] References Cited

U.S. PATENT DOCUMENTS

| | | |
|---|---|---|
| 1,257,297 | 2/1918 | Brown . |
| 1,639,815 | 8/1927 | Siebrandt . |
| 1,768,770 | 7/1930 | Kettelkamp . |
| 1,921,987 | 8/1933 | Ettinger . |
| 1,935,859 | 11/1933 | Putz .................................... 602/19 |
| 1,976,244 | 10/1934 | Moran . |
| 2,010,328 | 8/1935 | Siebrandt . |
| 2,187,323 | 1/1940 | Kelton . |
| 2,191,283 | 2/1940 | Longfellow . |
| 2,545,843 | 3/1951 | Cohan . |
| 2,661,000 | 12/1953 | Gazeley . |
| 2,687,129 | 8/1954 | Talkish ................................. 602/19 |
| 3,945,376 | 3/1976 | Kuehnegger ........................ 602/19 |
| 4,559,932 | 12/1985 | Salort ................................... 602/20 |
| 4,881,299 | 11/1989 | Young et al. . |
| 4,928,676 | 5/1990 | Pansiera . |
| 5,000,170 | 3/1991 | Young et al. . |
| 5,033,461 | 7/1991 | Young et al. . |
| 5,038,765 | 8/1991 | Young et al. . |
| 5,039,247 | 8/1991 | Young et al. . |
| 5,046,490 | 9/1991 | Young et al. . |
| 5,383,844 | 1/1995 | Munoz et al. . |
| 5,385,536 | 1/1995 | Burkhead et al. . |

FOREIGN PATENT DOCUMENTS 597623  3/1937  European Pat. Off. .

OTHER PUBLICATIONS

Brochure for "SAS Shoulder Arm System", 1988.
Brochure for "Ultralight Airplane Abduction Splint", 1987.
Brochure for "Masterhinge Shoulder Brace", 1991.
Advertisement "Quadrant Shoulder Brace", O&P Business News, Jan. 15, 1993.
"Gunslinger Shoulder Orthoses Off the Shelf", JOSPT, vol. 15, No. 2, Feb. 1992.
Advertisement for "A–Line Shoulder Orthosis".
Brochure for "Arm Abduction Inflatable Orthesis".
Brochure for "Abductor".
Brochure for "Durr Fillauer–Harvey–Armabductie-Orthese".

*Primary Examiner*—Linda C. Dvorak
*Attorney, Agent, or Firm*—Price, Gess & Ubell

[57] ABSTRACT

An orthopaedic shoulder brace that is adapted to evenly distribute weight onto a patient's waist and hip is disclosed. The shoulder brace includes a first anatomically-conforming shell having an upper curved portion for comfortably fitting around a right side of the waist of a user, and having a lower curved portion for comfortably fitting onto the right hip of the user. A second anatomically-conforming shell is also included which has an upper curved portion for comfortably fitting around a left side of the waist of the user, and which has a lower curved portion for comfortably fitting onto the left hip of the user. A strap connects the front portions of the first anatomically-conforming shell and the second anatomically-conforming shell, and a joining shell connects the back portions of the two shells. The joining shell is rotatably connected to the first anatomically-conforming shell at a first joint and rotatably connected to the second anatomically-conforming shell at a second joint. These two joints allow the first and second anatomically-conforming shells to rotate to accommodate the varying hip sizes of different users. Additionally, a scapulary panel is disclosed for applying pressure to the scapula near the injured shoulder of the user. The scapulary panel is adjustable across an area of the user's back.

18 Claims, 3 Drawing Sheets

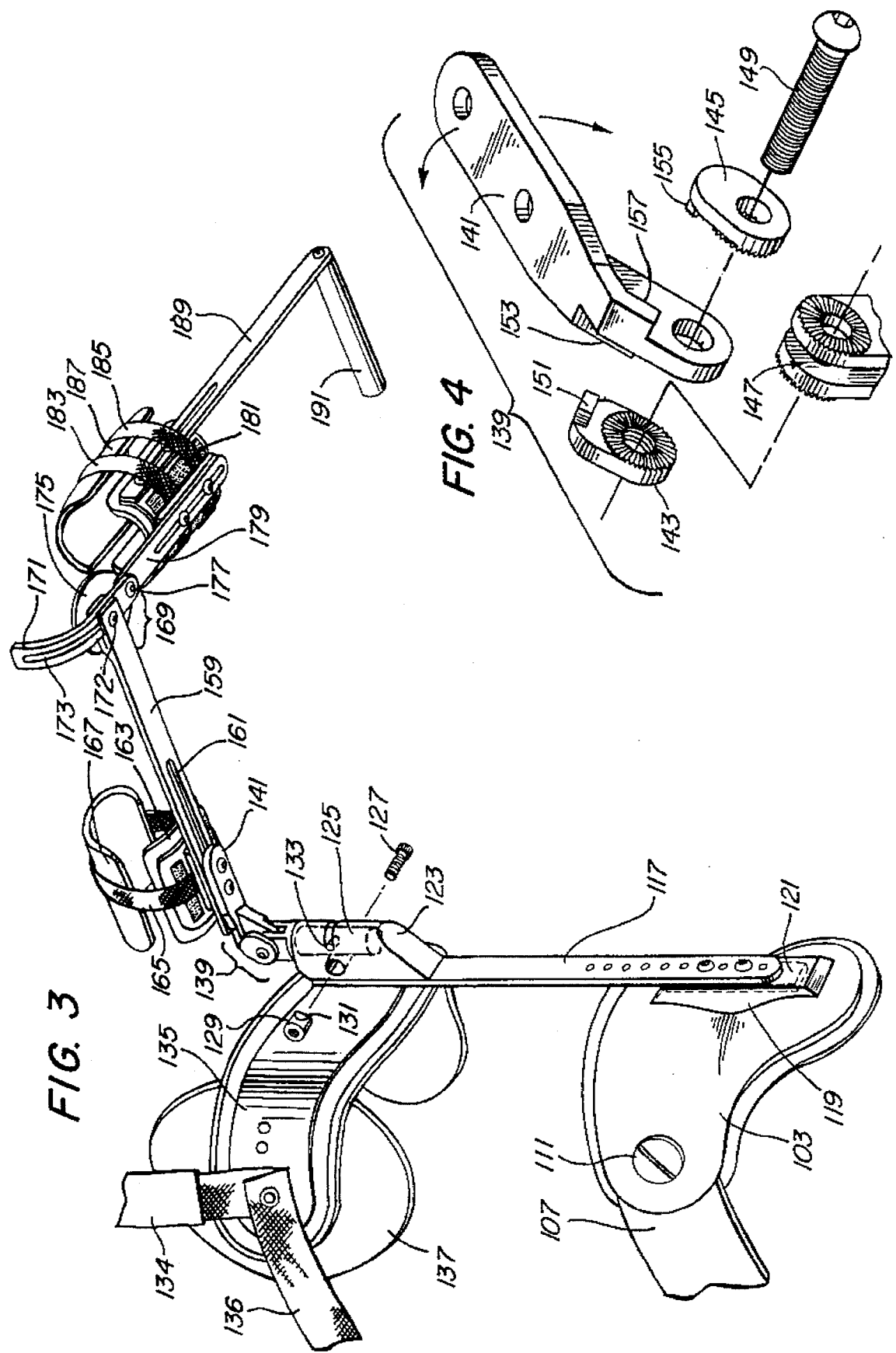

ORTHOPAEDIC SHOULDER BRACE HAVING ADJUSTABLE PELVIC, SCAPULARY, AND ARM SUPPORTS

BACKGROUND OF THE INVENTION

1. Field of the Invention

The present invention generally relates to a shoulder brace and, in particular, relates to orthopaedic braces which permit a limited range of movement of a limb or other body part and which includes an adjustable scapula containment pad.

2. Description of Related Art

Orthopaedic braces are often designed to provide both support and limited movement to injured shoulders. Many shoulder injuries require bracing during healing. The structure of an orthopaedic brace preferably should augment the structure or function of the injured arm or shoulder joint in order to promote healing.

In addition to providing support, orthopaedic braces often provide limited movement. Shoulder braces, for example, may provide for such limited movement in many planes. These shoulder braces frequently provide for flexion/extension, abduction/adduction, and rotational movement over a wide range of motion. Such movements of a joint through preselected ranges of motion are frequently advised for chronic conditions and for rehabilitation after surgery.

One treatment for a weakened shoulder, such as weakness caused by poliomyelitis or other nerve lesions, is to immobilize the arm in an elevated position. Treatment for this condition often includes keeping the arm in the elevated position to prevent overstretching of the deltoid muscle. The deltoid muscle controls vertical abduction (elevation) of the arm. If the arm is not maintained in an elevated position, the deltoid may be stretched beyond its elastic limit to the point where it is permanently damaged.

Existing shoulder braces provide both support and limited movement to injured joints and limbs. The support is often provided through a rigid structure and framework that adequately prevents movement of the arm, and the limited movement is often provided through adjustable structures that allow various components of the shoulder brace to be moved through various positions. Shoulder braces of the prior art, while providing support and limited movement, often comprise numerous metal and plastic parts and, accordingly, can be cumbersome and uncomfortable. In achieving the desired support and limitation of movement of a joint or limb, shoulder braces of the prior art often introduce a countereffect of focusing a significant amount of the weight of the shoulder brace onto one side of the waist of the patient.

Many prior-art shoulder braces include waist belts, which are attached at a point to the shoulder brace, and which introduce unnecessary discomfort and risk of injury. These belts focus the weight of the shoulder brace, as well as the weight of the patient's arm, onto the waist of the patient. This distribution is often uneven, occurring along the waistline of the patient, instead of having an even distribution along the waistline and the hips of the patient. Additionally, this distribution is often unevenly concentrated at the point of the attachment of the shoulder brace, which is usually on one side of the patient's waist.

Further, these belts, which often require the patient to bear some of the weight of the shoulder brace on the patient's shoulder and ribs, often do not provide a rigid lower-back support, and conceivably may contribute to lower-back injuries.

A problem of providing adequate means for supporting the scapula of a patient also exists in the prior art. The scapula is the large, flat, triangular bone forming the back part of the shoulder. When a patient's arm is placed into abduction (raised), the scapula is often not adequately supported by shorter braces of the prior art. The ligaments and tendons near the scapula, which are often tight after surgery, are accordingly not stretched during abduction of the arm. A problem thus exists in the prior art for providing adequate support for the scapula during abduction of the arm, to allow for stretching of ligaments and tendons near the scapula.

OBJECTS AND SUMMARY OF THE INVENTION

The present invention provides, an orthopaedic shoulder brace that is adapted to evenly distribute weight onto a patient's waist and hip. The shoulder brace alleviates potential risks of lower-back injury and pressure sores, and additionally provides enhanced comfort for the user.

The orthopaedic shoulder brace of the present invention includes a belt for distributing the weight of both the shoulder brace and the user's arm onto the user's waist and hips. This orthopaedic belt is adjustable for accommodating the varying hip sizes of different users. For example, a single belt can be adjusted to fit the typically narrower hips of men, and can also be adjusted to fit the typically wider hips of women.

This orthopaedic belt includes a first anatomically-conforming shell having an upper curved portion for comfortably fitting around a right side of the waist of a user, and having a lower curved portion for comfortably fitting onto the right hip of the user. A second anatomically-conforming shell is also included which has an upper curved portion for comfortably fitting around the left side of the waist of the user, and which has a lower curved portion for comfortably fitting onto the left hip of the user. A strap connects the front portions of the first anatomically-conforming shell and the second anatomically-conforming shell, and a joining shell connects the back portions of the two shells. The joining shell is rotatably connected to the first anatomically-conforming shell at a first joint and rotatably connected to the second anatomically-conforming shell at a second joint. These two joints allow the first and second anatomically-conforming shells to rotate, to thereby accommodate varying hip sizes.

A scapulary panel is also provided by the present invention. The scapulary panel applies pressure to the scapula near the injured shoulder of the user. The scapulary panel is adjustable across an area of the user's back. This scapulary panel contains the scapula when the arm goes into abduction, thus preventing the scapula from migrating out with abduction of the arm. The ligaments and tendons near the scapula are thus stretched by the lifting of the arm and the simultaneous containment of the scapula by the scapulary panel.

BRIEF DESCRIPTION OF THE DRAWINGS

The features of the present invention, which are believed to be novel, are set forth with particularity in the appended claims. The present invention, both as to its organization and manner of operation, may best be understood by reference to the following description, taken in connection with the accompanying drawings.

FIG. 3 is a schematic illustration of an underside view of the orthopaedic shoulder brace of the present invention;

FIG. 4 is a schematic diagram illustrating the supporting hinge of the orthopaedic shoulder brace of the present invention;

DETAILED DESCRIPTION OF THE PREFERRED EMBODIMENTS

The following description is provided to enable a person skilled in the art to make and use the invention and sets forth the best modes contemplated by the inventor of carrying out his invention. Various modifications, however, will remain readily apparent to those skilled in the art.

Figure 1:
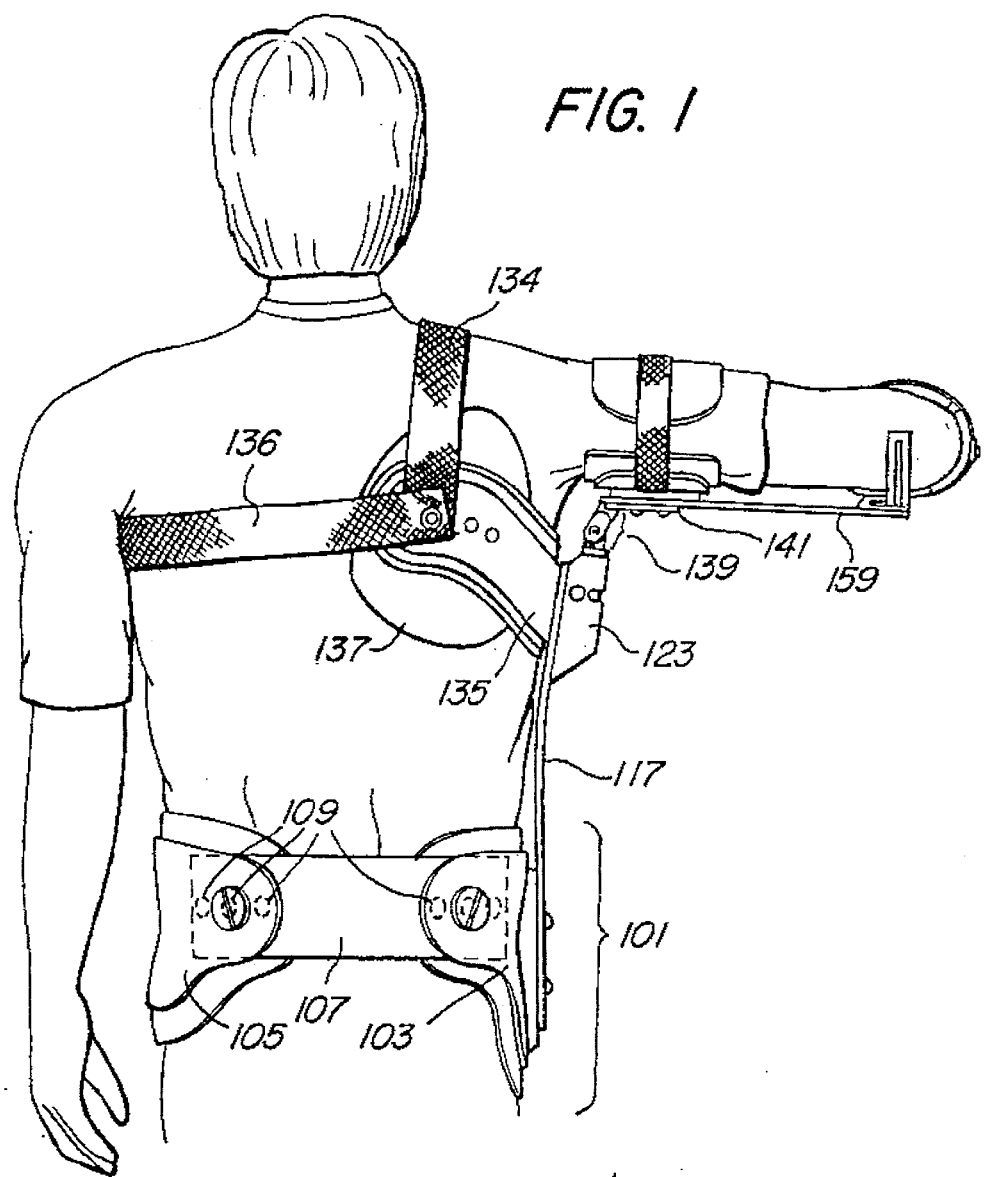
FIG. 1 is a schematic diagram illustrating a rear view of the orthopaedic shoulder brace of the present invention.

Turning to FIG. 1, the pelvic section 101 of the orthopaedic shoulder brace 102 of the present invention has two sides: the affected side 103 and the unaffected side 105. As illustrated, the affected side is the right side, but the left side may also be the affected side. A joining panel 107 is preferably formed from a semirigid low density polyethylene material. The joining panel 107 joins the two sides, and is adjustable via different holes 109 in the joining panel 107 to accommodate waists of different circumferences. The brace and the arm are thus supported by the pelvis and the hips instead of being suspended by straps that extend across the opposite shoulder.

Figure 2:
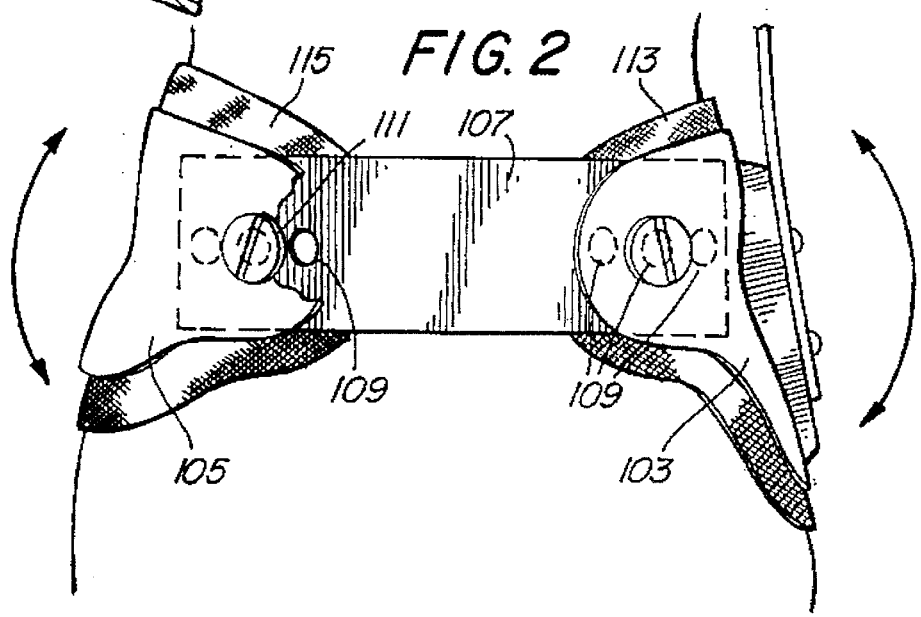
FIG. 2 is a schematic diagram illustrating the pelvic portion of the orthopaedic shoulder brace of the present invention on a user with wide hips.

FIG. 2 shows the pelvic section 101 on a user with wide hips. Each of the two sides 103 and 105 is pivotally connected to the joining panel 107 at a corresponding hole 109 in the pelvic section. This pivotal connection of each pelvic section to the joining panes allows for adjustment for differences in pelvic sizes. Thus, a user with narrow hips may comfortably wear the pelvic section 101, as shown in FIG. 1, and a user with wider hips may comfortably wear the same pelvic section 101 upon rotation of the affected side 103 and the unaffected side 105 about their respective bolts 111.

As shown in FIG. 2, the two sides 103 and 105 are pivoted about bolts 111 to accommodate larger hips. The ability of the pelvic section 101 to thus accommodate different waist and hip sizes allows for a distribution of the weight of the orthopaedic shoulder brace and the user's affected arm upon both of the user's hips. Additionally, the rigidity of the pelvic section 101 further provides a distribution of this weight. In the prior art, shoulder braces often distributed over 80% of the brace and arm weight on the affected side of the user. The user would, accordingly, develop pressure sores at the contact places on the affected hip. In contrast, the orthopaedic shoulder brace of the presently-preferred embodiment distributes approximately 60% of the brace and arm weight on the affected hip side, and distributes 40% of this weight on the other side. This distribution of brace and arm weight is an advantage not realized by the prior art.

In an alternative embodiment, additional weight distribution can be achieved by increasing the stiffness at the two rotation points 111. For example, these two pivot points may be adjusted and then locked, using a frictional interface such as teeth, at the adjusted position. For example, teeth may be provided on the joining panel 107 and on each of the sides 103 and 105 to thus provide a firm locking mechanism when the bolts 111 are tightened. Washers may be placed between the teeth to disable this locking mechanism.

The convenient adjustability feature eliminates any need for different pelves components for both males and females. The presently-preferred embodiment has three different sizes of pelvic sections, which accommodate all sizes. As shown in FIG. 2, the joining panel 107 has three holes 109 on each side. The affected side 103 and the unaffected side 105 may be joined to the joining panel 107 at any of the three corresponding holes 107. Any conventional joining means may be used. In the presently-preferred embodiment, a bolt and washer are used to join the respective members. The bolt 111 fits through the hole 109, which is illustrated by dotted lines, and fastens into a nut (not shown) having a thin profile.

Each of the pelvic section sides 103 and 105 has a corresponding pad 113 and 115, which separates the pelvic section side from the user. In the presently-preferred embodiment, these pads are fastened to the pelvic section sides with VELCRO®. Other fastening means may similarly be used.

Each of the affected side 103 and the unaffected side 105 is formed from a heat molding process in the presently-preferred embodiment. A flat sheet of plastic is heated and molded into the shape shown in FIG. 2.

Another view of the affected side 103 is shown in FIG. 3. The plastic member 103 comprises a curved portion and a rectangularly rigid portion, which provides a fastening means for the upright portion 117. The rectangularly rigid portion 119 protrudes from the curved portion, as a result of the heat molding process, and houses a bolt housing plate 121, which is preferably made from a metallic substance. The heat molded side 103 is made from a plastic in the presently-preferred embodiment, and is semirigid in the curved portion and significantly more rigid in the rectangularly rigid portion 119. The rectangularly rigid portion 119 additionally draws support from the bolt housing plate 121.

Looking back at FIG. 1, the upright portion 117 is connected to the affected pelvic sections 103, and has an adjustability means for adjusting the height of a user's arm. This adjustability means may comprise slots (not shown), or may comprise holes (FIG. 3). Two holes in the affected pelvic side 103 fit into any two of a plurality of holes in the upright portion 117.

At the top of the upright portion is a cylindrical member, the axillary hinge 123. This axillary hinge has a pin or cylinder 125 that fits inside the hinge. The pin 125 allows for anterior flexion. An Allen screw 127 in the axillary hinge can be loosened by an Allen wrench, and the brace can be rotated about an axis formed by the pin 125. The Allen screw 127 can then be tightened at the desired position. The Allen screw 127 threads into a locking nut 129 having a curved portion 131 which frictionally abuts with a portion of the pin 125, when the Allen screw 127 is tightened into the locking nut 129.

The arm of a user in the brace may be moved forward and backward along a 110-degree arc in the presently-preferred embodiment. A movement limiter 133 is attached to the pin 125. The movement limiter such as a pin 133 fits into a slot in the axillary hinge 123. The movement limiter 133 moves with the pin 125, and prevents rotation beyond a predetermined range according to the length of the slot in the axillary hinge 123. This movement may, however, be configured to accommodate other ranges of motion.

A thoracic band 135 is connected to the upright portion near the axillary hinge 123. The thoracic band 135 is flexible to accommodate different sizes of users. A plastic scapula containing panel 137 is adjustably attached to the thoracic band 135. The scapula containing panel 137 is adjustable along a direction generally parallel with the thoracic band 135. The scapula containing panel 137 contains the scapula when the arm goes into abduction (raised), thus preventing the scapula from migrating out with the arm. The scapula is the large, flat, triangular bone forming the back part of the shoulder. The ligaments and tendons near the scapula, which are often tight after surgery, are thus stretched by the lifting of the arm and the simultaneous containment of the scapula by the containing panel.

In the presently-preferred embodiment, the scapula containing panel 137 is secured to the thoracic band 135 via two bolts which feed through to respective holes in the thoracic band 135. The scapula containing panel 137 is adjustable along a length of the thoracic band 135 via a series of holes in the scapula containing panel 137. Thus, the two bolts in the thoracic band 135 may be placed in any two of the series of holes in the scapula containing panel 137 to move the scapula containing panel 137 along the length of the thoracic band 135. A rivet in the thoracic band 135 holds a shoulder strap 134, which fastens over the user's affected shoulder, and a torso strap 136, which fastens around the torso of the user's unaffected side (FIG. 1).

Figure 5:
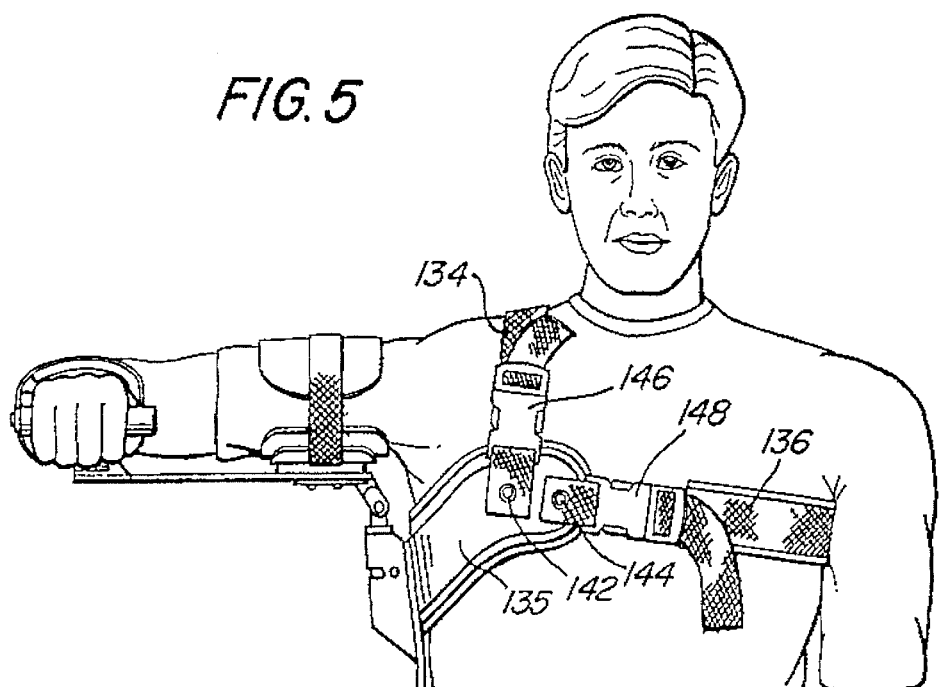
FIG. 5 is a schematic diagram illustrating a front view of the orthopaedic shoulder brace of the present invention.

A front view of the orthopaedic shoulder brace of the presently-preferred embodiment is shown in FIG. 5. The thoracic band 135 wraps around approximately half of the torso of the user's front affected side. Two rivets 142 and 144 secure buckles for the two respective straps 134 and 136. The shoulder strap 134 has a buckle 146 which allows for adjustment, and the torso strap 136 has a buckle 148 which similarly allows for adjustment.

Connected to the axillary hinge is a supporting hinge 139, as shown in FIG. 3. The supporting hinge 139 is connected to the top of the pin 125 and supports an extending member 141, which can be pivoted in a vertical plane about the supporting hinge. In addition to being pivotable in a vertical plane about the supporting hinge, the extending member 141 is rotatable in a horizontal plane which is perpendicular to the upright portion 117. Since the supporting hinge 139 and the extending member 141 are connected to the pin 125, rotation of the extending member 141 corresponds to rotation of the pin 125 within the axillary hinge 123.

The supporting hinge 139 and the extending member 141 are shown in FIG. 4. The supporting hinge 139 comprises the extending member 141, an upward movement locking-means 143, a downward movement locking-means 145, a locking-means accommodating portion 147, and an Allen screw 149. The Allen screw 149 is inserted through the five holes of the respective members, as shown in FIG. 4. The lower portion of the extending member 141 fits between the two portions of the locking-means accommodating portion 147 such that the three holes line up. The upward movement locking-means 143 fits against an outer side of the locking-means accommodating portion 147, and the downward movement locking-means 145 fits against the other outer side of the locking-means accommodating portion 147, such that their respective holes line up for insertion of the Allen screw 149. The upward movement locking-means 143 is rotatably adjustable about an axis formed by the Allen screw 149.

As mentioned, the extending member 141 may be moved in a vertical plane about the support hinge 139. This movement may be limited to a certain range or stopped altogether. The upward movement stopping protrusion 151 of the upward movement locking-means 143 can be adjusted to fit against the upward movement stopping ledge 153 of the extending member 141. In such a case, the extending member 141 cannot rotate upward. If the upward movement locking-means 143 is locked in a position which places the upward movement stopping protrusion 151 in a position above the upward movement stopping ledge 153, then the extending member 141 may be moved higher in the vertical plane until the upward movement stopping ledge 153 comes into contact with the upward movement stopping protrusion 151. Similarly, a downward movement stopping protrusion 155 on the downward movement locking-means 145 may be rotated to come into contact with the downward movement stopping ledge 157. Such a contact prevents the extending member 141 from rotating downward.

Both the upward movement locking-means 143 and the downward movement locking-means 145 may be rotated when the Allen screw 149 is loosened. When the Allen screw 149 is tightened, the teeth on each of the respective upward movement locking-means 143 and downward movement locking-means 145 come into contact with the teeth of the locking-means accommodating portion 147. Thus, the upward movement stopping protrusion 151 and the downward movement stopping protrusion 155 may be locked into a position where the upward movement stopping ledge 153 and the downward movement stopping ledge 155 are contacted. This configuration prevents any movement of the extending member 141 in the vertical plane. Either or both of the upward movement stopping portion 153 and the downward movement stopping portion 155 may be adjusted and locked in a position away from their respective stopping ledges 153 and 157 to provide for rotation of the extending member 141 within the limits set by the respective stopping protrusions 151 and 155.

An upper-arm support 159 is adjustably connected to the extending member 141. This upper-arm support 159 comprises a slot 161 which extends along a length of the upper-arm support 159 from a portion near the supporting hinge 139 to a portion near the middle of the upper-arm support 159. An upper-arm platform 163 is secured to the extending member 141 via two bolts. These two bolts extend from the upper-arm support 159 through the slot 161 in the upper-arm support 159 and into the extending member 141. The two bolts can be loosened, thereby allowing these two bolts to slide along the slot 161 in the upper-arm support 159. Since these two bolts are connected to the axillary hinge 123 through the supporting hinge 139, the upper-arm support 159 must move relative to the axillary hinge 123 in order for the two bolts to slide in the slot 161. Thus, the length of the upper-arm support 159 can be increased or decreased to accommodate different patients by sliding the upper-arm support 159 along the two bolts. An adjustable strap 165, having a pad 167 attached thereto and connected to the upper-arm platform 163, can be wrapped around a user's arm and connected back to the upper-arm platform 163 via a fastening means such as VELCRO®.

An elbow-pivoting assembly 169 is connected to the distal end of the upper-arm support 159. This elbow-pivoting assembly 169 includes a curved sliding member 171 having a slot 173. The curved member 171 is slidably connected to the distal end of the upper-arm support 159 by a bolt 172. The bolt 172 extends from the distal end of the upper-arm support 159 through the slot 173 and into an elbow platform 175.

When the curved member 171 is slid about the bolt 172, the curved member 171 moves relative to the distal end of the upper-arm support 159. Since the curved member 171 is slidably connected to the distal end of the upper-arm support 159 in a perpendicular fashion, movement of the curved member 171 causes a user's lower arm to rotate in a perpendicular plane relative to the upper-arm support 159. The lower arm of a user may be moved along a 90-degree arc in the presently-preferred embodiment.

The present invention may be configured to accommodate other ranges of motion. The bolt 172 has an Allen wrench head in the presently-preferred embodiment and may be loosened for adjustment of the curved member 171 and then tightened at a desired angle.

The curved member 171 is rotatably connected to a lower-arm support 179 via a bolt 177. The bolt 177 extends through a hole in the curved member 171, which is distinct from the slot 173, into a hole in the lower-arm support 179. This lower-arm support 179, in addition to rotating with the curved member 171, can be rotated about bolt 172 in a parallel plane relative to the upper-arm support 159 about the bolt 177. This rotation within the parallel plane causes a user's lower arm to move toward the user and away from the user. The range of rotation in the presently-preferred embodiment is close to 360 degrees. Where the portion of the curved sliding member 171 comes into contact with the portion of the lower-arm support 179, teeth are provided (not shown). Thus, when the bolt 177 is tightened, the teeth of the two respective members come into contact and prevent rotation of the lower-arm support 179 with respect to the curved sliding member 171. This teeth-locking mechanism is similar to that described with regard to FIG. 4.

A lower-arm platform 181 is connected to the lower-arm support 179 via two bolts. The lower-arm platform 181 is configured to comfortably support a user's lower arm and hand. The lower-arm support 179 comprises a slot, along which the two bolts and the lower-arm platform 181 attached thereto may slide. The sliding of the lower-arm platform 181 and the bolts along the slot allow the length from the elbow assembly 169 to the lower-arm platform 181 to be adjusted by loosening and tightening the bolts, preferably with an Allen wrench. Thus, users having different lower-arm lengths may comfortably be accommodated by the present invention. Two adjustable straps 183 and 185, having a pad 187 attached thereto and connected to the lower-arm platform 181, can be wrapped around a user's arm and connected back to the lower-arm platform 181 using a conventional fashioning means such as VELCRO®.

The lower-arm platform 181 comprises two holes for accommodating an adjustable bar 189 via two bolts. The adjustable bar 189 has a handle 191 attached thereto for a user to grasp. The adjustable bar 189 preferably has a slot, which accommodates two bolts in the lower-arm platform, and which allows the adjustable bar 189 to accommodate users having different forearm lengths.

Figure 6:
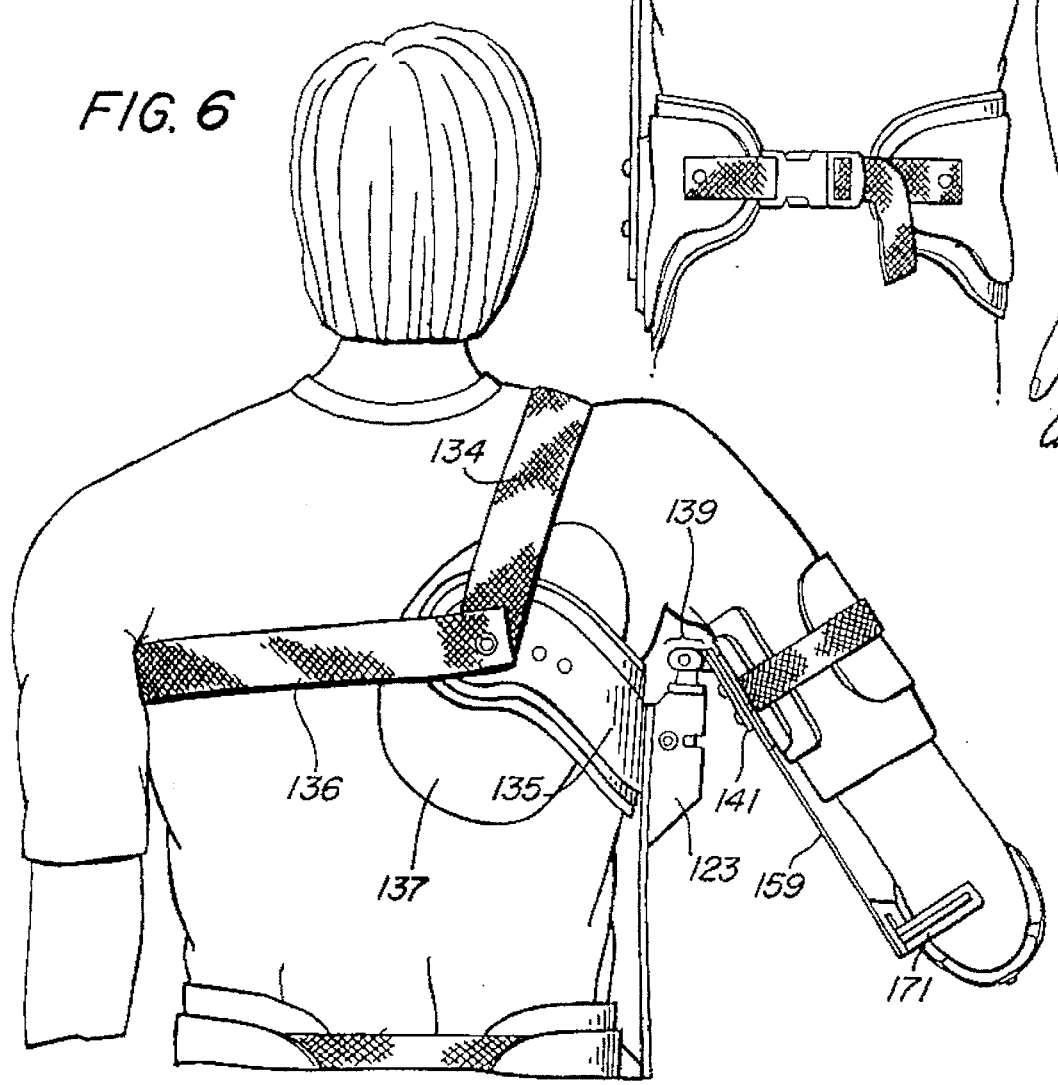
FIG. 6 is a schematic diagram illustrating a rear view the orthopaedic shoulder brace of the present invention.

AS shown in FIG. 6, the shoulder brace of the present invention can be adjusted to lower a user's arm to his side. This position is accomplished by lowering the adjustable upright portion 117, which is attached to the affected pelvic side 103. Additionally, the extending member is rotated via the supporting hinge 139, and the elbow-pivoting assembly 169 is adjusted to outwardly extend the user's lower arm slightly. This position does not usually require the scapula containing panel 137, and does not require any additional parts, a feature unavailable in the prior art.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A shoulder brace adapted to adjustably support a scapula of a user and to adjustably distribute weight onto a user's waist and hip, comprising:
   a pelvic belt having two rigid shells, each shell conforming to a waist and hip of the user and being adjustable to accommodate different hip sizes of different users;
   a thorax band adapted to be wrapped around a portion of the user's torso beneath a shoulder of the user;
   a support connected to one of the rigid shells for connecting the pelvic belt to the thorax band, and adapted to support an arm rest; and
   a scapulary containing panel connected to the thorax band for applying pressure to a scapula of the user, the scapulary containing panel being adjustable along the thorax band and across an area of the user's back.

2. The shoulder brace adapted to adjustably support a scapula of a user according to claim 1, the pelvic belt including a joining shell for connecting the two rigid shells.

3. The shoulder brace adapted to adjustably support a scapula of a user according to claim 1, each of the two shells having an upper curved portion for comfortably fitting around a side of a waist of the user.

4. The shoulder brace adapted to adjustably support a scapula of a user according to claim 3, each of the two shells having a lower curved portion for comfortably fitting onto a corresponding hip of the user.

5. The shoulder brace adapted to adjustably support a scapula of a user according to claim 4, the pelvic belt including means for extending over a front side of the user and for connecting the two shells.

6. The shoulder brace adapted to adjustably support a scapula of a user according to claim 5, the pelvic belt including a joining shell for extending over a back side of the user, the joining shell rotatably connected to each of the two shells.

7. The shoulder brace adapted to adjustably support a scapula of a user according to claim 6, the joining shell being rotatably connected to a first one of the two shells at a first joint and being rotatably connected to a second one of the two shells at a second joint, wherein the first joint and the second joint can be locked to prevent rotation and add rigidity.

8. The shoulder brace adapted to adjustably support a scapula of a user according to claim 7, the first and the second joints allowing the first and second shells to rotate to accommodate varying hip sizes of different users.

9. An orthopedic shoulder brace adapted to adjustably support a scapula of a user, comprising:
   distributing means for distributing weight onto a user's waist and hips;
   wrapping means for wrapping around a portion of the user's torso beneath an injury of the user;
   connecting means connected to the distributing means for connecting the distributing means to the wrapping means and for supporting an arm rest; and
   applying means detachably connected to the wrapping means for applying pressure to a scapula of the user in order to hold the scapula in place when an arm of the user corresponding to the scapula is raised, the applying means being adjustable across an area spanning a portion of a length of the wrapping means.

10. The shoulder brace adapted to adjustably support a scapula of a user according to claim 9, the applying means being adjustable across an area spanning a portion of a length of the wrapping means.

11. The shoulder brace adapted to adjustably support a scapula of a user according to claim 9, the distributing means and the wrapping means being rigid.

12. The shoulder brace adapted to adjustably support a scapula of a user according to claim 9, the applying means being adjustable across a length of the distributing means.

13. A shoulder brace for adjustably supporting an arm, comprising:
   a belt for wrapping around a user's waist;
   a rigid member extending from a first point on the belt to a second point beneath a shoulder of the user;
   a cylinder housing for rotatably housing a cylinder at the second point, the cylinder being rotatable about a substantially vertical axis and having an upper end, the cylinder housing having a slot accommodating a limiter pin attached to the cylinder, the limiter pin sliding within the cylinder housing when the cylinder is rotated, wherein a range of rotation of the cylinder is limited by a length of the slot;
   an arm support pivotally connected to the upper end, the arm support being downwardly pivotable from a position where the arm support is substantially perpendicular to the rigid member to a position where the arm support forms an acute angle with the rigid member; and
   means connected to the rigid member for containing a scapula of a user when the arm of the user is placed into abduction, the containing means comprising a thorax band and a rigid panel adjustably and detachably connected to the thorax band.

14. The shoulder brace of claim 13, further including a lower arm support connected to the arm support, the lower arm support being pivotable in a plane perpendicular to the arm support.

15. A shoulder brace adapted to adjustably support a scapula of a user and to adjustably distribute weight onto a user's waist and hip, comprising:
   a pelvic belt having a left rigid shell and a right rigid shell, each of the two rigid shells having an upper curved portion for comfortably fitting around a side of a waist of the user and having a lower curved portion for comfortably fitting onto a hip of the user, each of the two rigid shells being rotatably connected to a joining shell to accommodate different hip sizes of different users;
   a thorax band for wrapping around a portion of the user's torso beneath an injury of the user, the portion extending from a front side of the user's torso to a rear side of the user's torso;
   a support connected to one of the rigid shells for connecting the pelvic belt to the thorax band, the support comprising means for supporting an arm rest; and
   a scapulary containing panel detachably connected to one of a plurality of locations along the thorax band for applying pressure to a scapula of the user.

16. A shoulder brace for adjustably supporting an arm, comprising:
   a belt for wrapping around a user's waist;
   a rigid member extending from a first point on the belt to a second point beneath a shoulder of the user;
   a cylinder housing for rotatably housing a cylinder at the second point, the cylinder being rotatable about a substantially vertical axis and having an upper end, the cylinder housing having means for stopping the rotation of the cylinder;
   an arm support pivotally connected to the upper end, the arm support being downwardly pivotable from a position where the arm support is substantially perpendicular to the rigid member to a position where the arm support forms an acute angle with the rigid member; and
   motion-limiting means connected between the upper end and the arm support, the motion-limiting means comprising a first adjustable stop means for contacting a first portion of the arm support to prevent the arm support from pivoting downward past a first predetermined angle, and further comprising a second adjustable stop means for contacting a second portion of the arm support to prevent the arm support from pivoting upward past a second predetermined angle, the first and second stop means being adjustable to provide from a 0-degree range of motion to a 110-degree range of motion of the arm support.

17. An orthopedic shoulder brace adapted to adjustably support a scapula of a user, comprising:
   distributing means for distributing weight onto a user's waist and hips, at least a portion of the distributing means being rigid;
   rigid wrapping means for wrapping around a portion of the user's torso beneath an injury of the user;
   connecting means connected to the distributing means for connecting the distributing means to the wrapping means and for supporting an arm rest; and
   applying means detachably connected to the wrapping means for applying pressure to a scapula of the user in order to hold the scapula in place when an arm of the user corresponding to the scapula is raised, the applying means being adjustable across a length of the rigid portion of the distributing means.

18. The shoulder brace adapted to adjustably support a scapula of a user according to claim 17, the applying means being adjustable across an area of the user's back.

* * * * *